US00PP16192P2

(12) United States Plant Patent
Hanes

(10) Patent No.: US PP16,192 P2
(45) Date of Patent: Jan. 10, 2006

(54) GERANIUM PLANT NAMED 'FREE LAVER TWO'

(50) Latin Name: *Pelargonium peltatum*
Varietal Denomination: Free Laver Two

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 116 days.

(21) Appl. No.: 10/818,338

(22) Filed: Apr. 5, 2004

(51) Int. Cl.
*A01H 5/00* (2006.01)

(52) U.S. Cl. ..... Plt./332
(58) Field of Classification Search ..... Plt./332
See application file for complete search history.

(56) References Cited

U.S. PATENT DOCUMENTS

PP11,720 P * 12/2000 Trees ..... Plt./332
PP13,230 P2 * 11/2002 Hanes ..... Plt./332

OTHER PUBLICATIONS

UPOV ROM GTITM Computer Database, GTI Jouve Retrieval Software 2004/04 Citations for 'Free Lave Two'.*

* cited by examiner

*Primary Examiner*—Howard J. Locker
*Assistant Examiner*—W. C. Haas
(74) *Attorney, Agent, or Firm*—C. A. Whealy

(57) ABSTRACT

A new and distinct cultivar of Ivy Geranium plant named 'Free Laver Two', characterized by its compact, low trailing, outwardly spreading and mounded growth habit; freely basal branching habit; freely flowering habit with many flower umbels per plant; flower umbels with large light violet-colored double flowers; and resistance to leaf oedema.

1 Drawing Sheet

Botanical designation: *Pelargonium peltatum.*
Variety denomination: 'Free Laver Two'.

BACKGROUND OF THE INVENTION

The present invention relates to a new and distinct cultivar of Geranium plant, botanically known as *Pelargonium peltatum,* commercially known as an Ivy Geranium, and hereinafter referred to by the name 'Free Laver Two'.

The new Ivy Geranium is a product of a planned breeding program conducted by the Inventor in Gilroy, Calif. The objective of the breeding program is to develop new Ivy Geranium cultivars with mounded plant habit, good basal branching, large flowers, attractive flower and foliage coloration and resistance to leaf oedema.

The new Ivy Geranium originated from a cross-pollination made by the Inventor in November, 2000 of two proprietary *Pelargonium peltatum* selections, not patented. The cultivar Free Laver Two was discovered and selected by the Inventor as a single flowering plant within the progeny from this cross-pollination in a controlled environment in Gilroy, Calif. in April, 2001.

Asexual reproduction of the new cultivar by terminal cuttings taken at Gilroy, Calif., since April, 2001 has shown that the unique features of this new Ivy Geranium are stable and reproduced true to type in successive generations of asexual reproduction.

SUMMARY OF THE INVENTION

The following traits have been repeatedly observed and are determined to be the unique characteristics of 'Free Laver Two'. These characteristics in combination distinguish 'Free Laver Two' as a new and distinct Ivy Geranium cultivar:

1. Compact, low trailing, outwardly spreading and mounded growth habit.
2. Freely basal branching habit.
3. Freely flowering habit with many flower umbels per plant.
4. Flower umbels with large light violet-colored double flowers.
5. Resistant to leaf oedema.

In side-by-side comparisons conducted in Gilroy, Calif., plants of the new Ivy Geranium differed from plants of the parent selections primarily in flower color.

The new Ivy Geranium can be compared to the cultivar, Freelight Lav Two, (U.S. Plant Pat. No. 13,230). However, in side-by-side comparisons conducted in Gilroy, Calif., plants of the new Ivy Geranium differed from plants of the cultivar Freelight Lav Two in the following characteristics:

1. Plants of the new Ivy Geranium had smaller leaves than plants of the cultivar Freelight Lav Two.
2. Leaves of plants of the new Ivy Geranium did not have a distinct zonation pattern whereas leaves of plants of the cultivar Freelight Lav Two had a distinct zonation pattern.
3. Plants of the new Ivy Geranium had larger flowers than plants of the cultivar Freelight Lav Two.
4. Flowers of plants of the new Ivy Geranium were darker in color than flowers of plants of the cultivar Freelight Lav Two.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Free Laver Two'.

The photograph at the bottom of the sheet is a close-up view of typical flowers, flower buds and leaves of 'Free Laver Two'. Flower and foliage colors in the photographs may differ slightly from the color values cited in the detailed botanical description which accurately describe the colors of the new Ivy Geranium.

DETAILED BOTANICAL DESCRIPTION

Plants of the cultivar Free Laver Two have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the summer with day temperatures ranging from 24 to 29° C., night temperatures ranging from 13 to 18° C. and light levels about 2,000 foot-candles. Plants used for the photographs and description were about five months from planting rooted cuttings. In the following description, color references are made to The Royal Horticultural Society Colour Chart, 1995 Edition, except where general terms of ordinary dictionary significance are used.

Botanical classification: *Pelargonium peltatum* cultivar Free Laver Two.

Parentage:

*Female parent.*—Proprietary *Pelargonium peltatum* selection, not patented.

*Male parent.*—Proprietary *Pelargonium peltatum* selection, not patented.

Propagation:

*Type cutting.*—Terminal cuttings.

*Time to initiate roots.*—About 12 to 14 days at 22° C.

*Time to develop roots.*—About 28 to 32 days at 22° C.

*Root description.*—Fibrous; white in color.

*Rooting habit.*—Freely branching.

Plant description:

*General appearance.*—Compact, low trailing, outwardly spreading and mounded growth habit.

*Growth and branching habit.*—Moderately vigorous to vigorous and freely basal branching with about five primary basal branches each with two to three secondary lateral branches per plant. Pinching, that is, removal of terminal apices, enhances branching.

*Plant height to top of foliage.*—About 12 cm.

*Plant height to top of flower umbels.*—About 18 cm.

*Plant width.*—About 38 by 60 cm.

*Lateral branches.*—Length: About 38 cm. Diameter: About 5 mm. Internode length: About 4.5 cm. Texture: Pubescent. Color: 146A.

*Foliage description.*—Arrangement: Opposite. Length: About 8 cm. Width: About 8 cm. Shape: Rounded palmate. Apex: Broadly acute. Base: Peltate to truncate. Margin: Five to seven lobes. Venation: Palmate. Texture, upper and lower surfaces: Slightly rough and coarse; glandular; pubescent. Color: Developing foliage, upper and lower surfaces: 144A. Fully expanded foliage, upper surface: 146A. Fully expanded foliage, lower surface: 146B. Venation, upper surface: 146C. Venation, lower surface: 146D. Petiole: Length: About 4.2 cm. Diameter: About 2 mm. Texture, upper and lower surfaces: Pubescent. Color, upper and lower surfaces: 146A.

Flower description:

*Flower arrangement and type.*—Double rounded flowers arranged in hemispherical umbels arising from apical leaf axils. Umbels displayed above the foliage. At full flowering, usually about 18 open and developing umbels per plant. Flowers not persistent; umbels persistent. Flowers not fragrant.

*Flowering season.*—Year-round under greenhouse conditions. In the garden, flowering is continuous from spring until fall. Plants start flowering about eight weeks after planting.

*Flower longevity.*—Flowers last about one week on the plant.

*Umbels.*—Height: About 6 cm. Diameter: About 9.5 cm. Number of flowers and flower buds per umbel: About ten. Flower diameter: About 4.5 cm. Flower depth (height): About 2.3 cm.

*Flower buds.*—Length: About 2 cm. Diameter: About 1.5 cm. Shape: Ovoid. Color: 75B.

*Petals.*—Quantity/arrangement: About 25 petals per flower in numerous whorls. Length: About 3.3 cm. Width: About 1.8 cm. Shape: Spatulate. Apex: Rounded. Base: Attenuate. Margin: Entire. Texture, upper and lower surfaces: Smooth; satiny. Color: When opening, upper surface: 84B. When opening, lower surface: 75D. Fully opened, upper surface: 84B; venation, outer petals, 74A to 78A; venation, center petals, 84B. Fully opened, lower surface: 75A; venation, outer petals, 78B; venation, center petals, 75D.

*Sepals.*—Quantity/arrangement: Five per flower in a single whorl; not imbricate on open flowers. Length: About 1.7 cm. Width: About 4 mm. Shape: Elliptical. Apex: Acuminate. Margin: Entire. Texture, upper and lower surfaces: Pubescent. Color, upper and lower surfaces: 146A.

*Peduncle* (*umbel stem*).—Length: About 16 cm. Diameter: About 3 mm. Angle: About 60 to 75° from vertical. Strength: Strong. Texture: Pubescent. Color: 146A.

*Pedicel* (*individual flower stem*).—Length: About 2.6 cm. Diameter: About 1.5 mm. Angle: Erect to about 90° from vertical. Strength: Strong. Texture: Sparsely pubescent. Color: 146A.

*Reproductive organs.*—Androecium: Anther quantity: About five to ten per flower. Anther length: Less than 1 mm. Anther shape: Oval. Anther color: 60D. Pollen amount: Scarce. Pollen color: 42C. Gynoecium: Pistil quantity: One per flower. Pistil length: About 9 mm. Stigma shape: Six-parted, star-shaped; reflexed. Stigma color: 71B. Style length: About 3 mm. Style color: 70C. Ovary color: 194C.

*Seed/fruit.*—Seed and fruit development has not been observed.

Disease/pest resistance: Resistance to pathogens and pests common to *Pelargonium* has not been observed.

Oedema resistance: Plants of the new Ivy Geranium have been observed to be resistant to leaf oedema when exposed to conditions conducive to leaf oedema development.

It is claimed:

1. A new and distinct cultivar of Ivy Geranium plant named 'Free Laver Two', as herein illustrated and described.

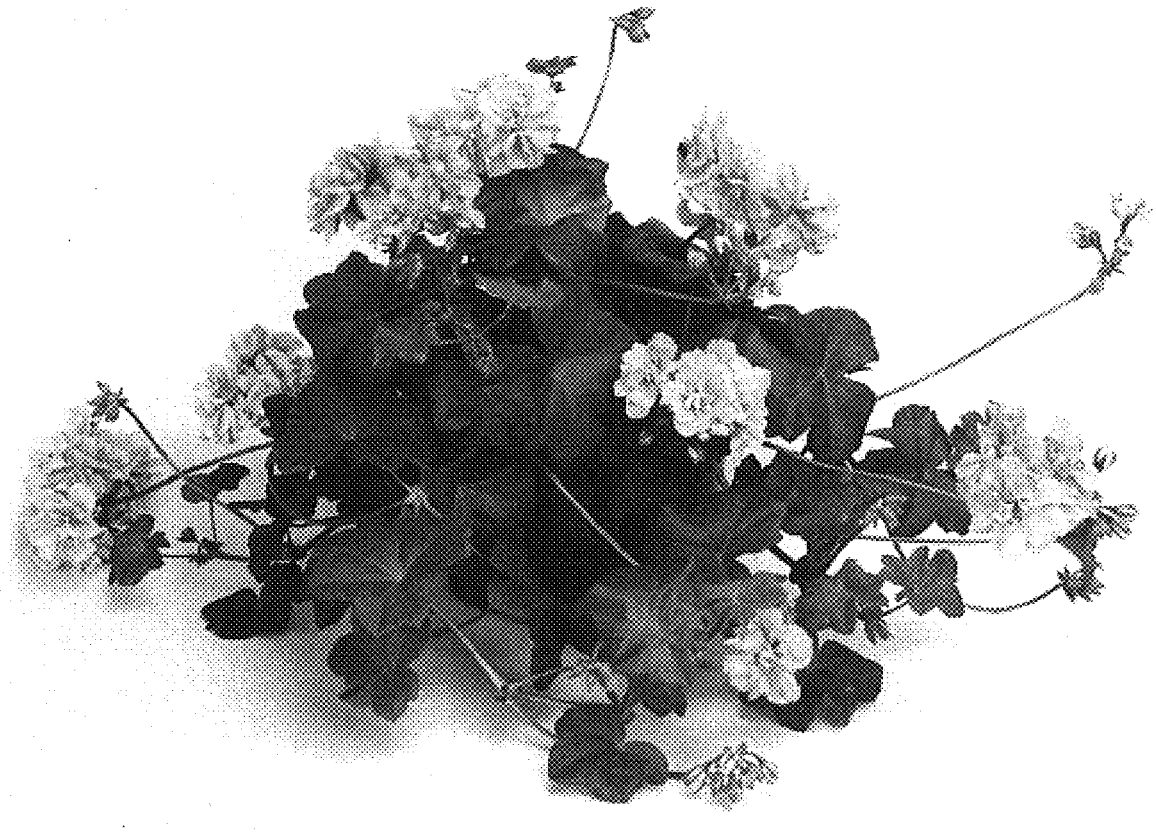
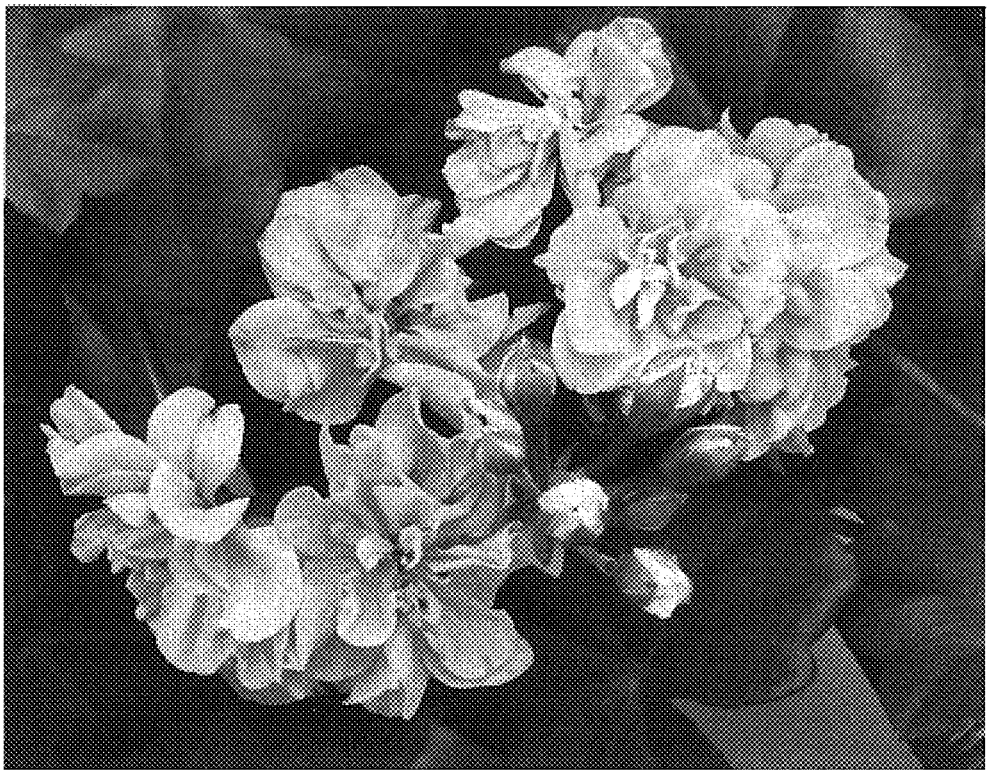

* * * * *